March 3, 1970 N. R. HAGFORS Re. 26,809

IMPLANTABLE ELECTRODE

Original Filed Oct. 20, 1966

INVENTOR.
NORMAN R. HAGFORS
BY Donald R. Stone
ATTORNEY

United States Patent Office

Re. 26,809
Reissued Mar. 3, 1970

26,809
IMPLANTABLE ELECTRODE

Norman R. Hagfors, Minneapolis, Minn., assignor to Medtronics, Inc., Minneapolis, Minn., a corporation of Minnesota Original No. 3,405,715, dated Oct. 15, 1968, Ser. No. 588,015, Oct. 20, 1966. Application for reissue Feb. 27, 1969, Ser. No. 806,751
Int. Cl. A61n *1/04*
U.S. Cl. 128—418 12 Claims

Matter enclosed in heavy brackets [ ] appears in the original patent but forms no part of this reissue specification; matter printed in italics indicates the additions made by reissue.

ABSTRACT OF THE DISCLOSURE

Electrode apparatus for stimulating an animal nerve, there being at least three electrodes, one of which is disposed between the other two, and the electrical connection being such that the two outside electrodes are in current guarding relation to the inner electrode, all to prevent stray current from stimulating adjacent nerves. The electrodes are embedded in a substance substantially inert to body fluids and tissue.

This invention relates to medical apparatus, and more particularly to an improved implantable electrode for electrical stimulation of a nerve within the body of an animal. The word animal is here used in its broad sense, including Homo sapiens.

The need for the apparatus of this invention is apparent upon consideration of such modern medical equipment as the carotid sinus nerve stimulator fully described in a co-pending application by Seymour I. Schwartz and Robert C. Wingrove, Ser. No. 397,899, entitled, Implantable Stimulator for Reducing Blood Pressure in Hypertensive Persons. In this co-pending application there is described the use of an implantable, artificial nerve stimulator, which provides electrical impulses for stimulation of the carotid sinus nerve to alleviate the problems of hypertensive animals.

An example of an implantable electrode is fully described in another co-pending application by Seymour I. Schwartz, Robert C. Wingrove and James A. Anderson, Ser. No. 512,981, entitled Implantable Electrode for Nerve Stimulation. This last named application describes the use of a pair of electrodes, suitable for implantation in the body of an animal. The electrodes are each formed to be connected to spaced points along a nerve, to provide electrical stimulation of the nerve from a source of signal energy to which the electrodes are connected by flexible leads. The electrodes and leads are made of an electrically conductive material inert to body fluids and tissues, and are encapsulated, except for the portion of the electrode surrounding the nerve, in another substance which is also inert to body fluids and tissue, as well as an electrical insulator.

One disadvantage of the above described two-electrode configuration is the limitation of maximum signal pulse which can be applied to the electrodes to stimulate the nerve. This maximum limitation is caused by stray currents which flow between the electrodes through body fluids and tissue, rather than through the nerve itself. If the stray currents reach a high enough level, adjacent nerves may be inadvertently stimulated. The apparatus of this invention overcomes this limitation by providing an electrode configuration which greatly eliminates stray currents by providing a plurality of electrically guarding electrodes placed around an electrically active electrode.

Briefly described, the apparatus of this invention comprises the use of guarding electrodes around an active electrode, all of which are connected to or around the desired nerve. In the specific embodiment to be described herein, a three-electrode configuration is used. Two of the electrodes are connected to a single electrical lead, and the third electrode is connected to another electrical lead. The electrical leads are connected to a source of signal energy such that the third electrode is the active electrode. The leads in the electrodes are placed in a specially formed encapsulating material substantially inert to body fluid and tissue, and the leads and electrodes themselves are made of material substantially inert to body fluids and tissue. A portion of each of the three electrodes is left unencapsulated, to be connected directly to the desired nerve itself. These portions of each electrode are connected to a nerve in spaced relation, such that the third or active electrode is placed between the other two electrodes. Therefore, current flowing in either direction from the active electrode will pass through the nerve to the guard electrodes, rather than pass through body fluids or tissue surrounding the electrode apparatus.

Figure 1:
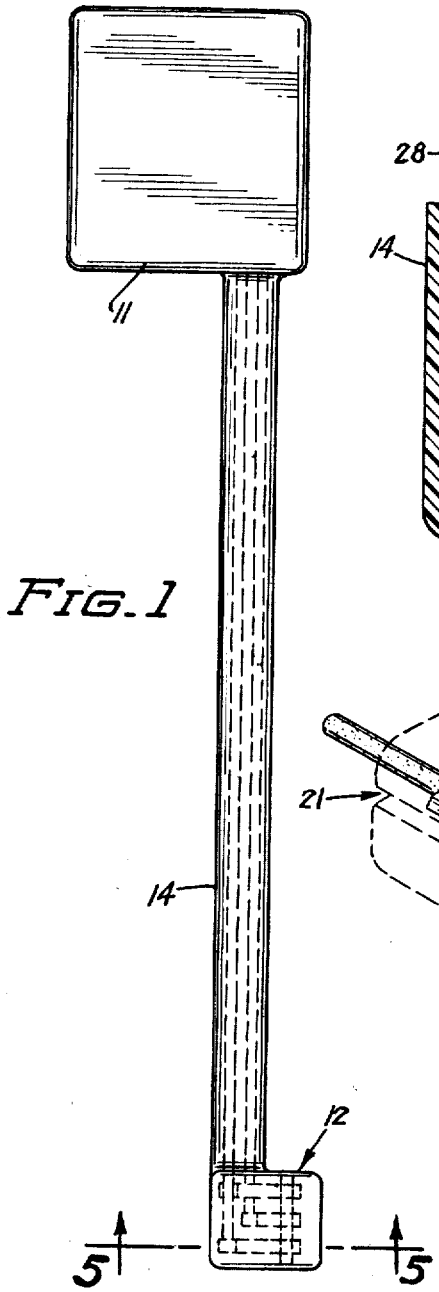
FIGURE 1 is a view of an embodiment of this invention which can be used with an implantable source of electrical signal energy.

FIGURE 1 discloses an embodiment of this invention having a head indicated generally at 12, a tail 14 connected to head 12 and also connected to a source of electrical signal energy 11.

Figure 2:
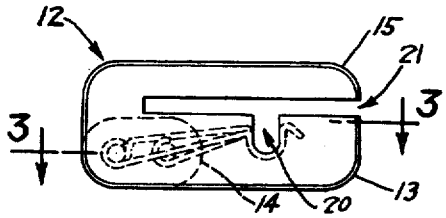
FIGURE 2 is a side view of the embodiment of FIGURE 1 showing the head of the embodiment having a slot forming an upper and lower layer.

FIGURE 2 is a side view of head 12 disclosing a slot 21 in head 12 forming an upper layer 15 and a lower layer 13. A groove 20 is shown in lower layer 13.

Figure 3:
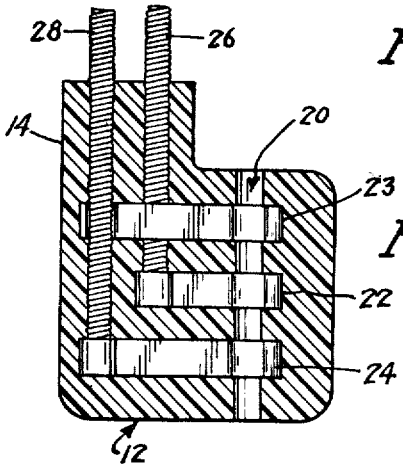
FIGURE 3 is a sectional view of FIGURE 2, taken along the line 3—3.

FIGURE 3 discloses a plurality of electrodes 22, 23 and 24, partially encapsulated in the substance of lower layer 13, and partially formed to groove 20. A pair of leads 26 and 28, here shown as coiled lengths of an electrically conductive material, are encapsulated in the substance of tail 14 and head 12. Lead 26 is connected to electrode 22, while lead 28 is connected to electrodes 23 and 24.

Figure 4:
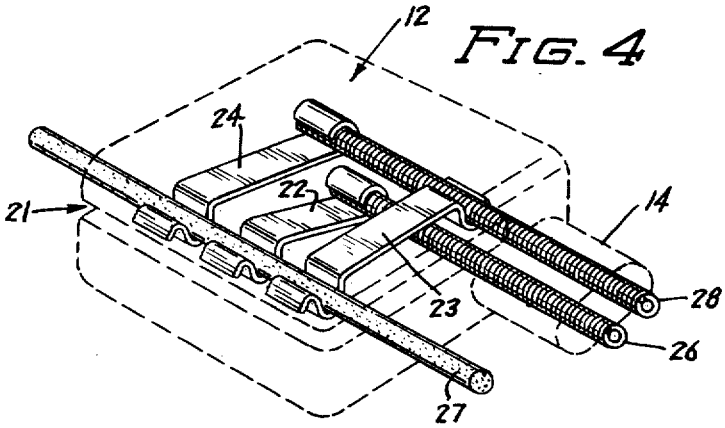
FIGURE 4 is a perspective view of the head portion of the embodiment of FIGURE 1.

FIGURE 4 is a perspective view which discloses electrodes 22, 23 and 24 connected to spaced points along the length of a nerve or nerve fiber 27, such as the carotid sinus nerve.

Figure 5:
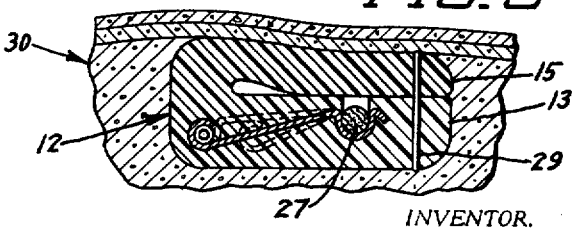
FIGURE 5 is a sectional view of the embodiment of FIGURE 1 taken along the line 5—5, showing the embodiment connected to a nerve and implanted in the body of an animal.

FIGURE 5 again shows nerve 27 within groove 20 with upper layer 15 fastened to lower layer 13 by sutures 29. Head 12 is shown in FIGURE 5 as being implanted in the body 30 of an animal.

Because this invention comprises a plurality of electrodes which are to be implanted within the body of an animal, it is necessary that the substance which comprises head 12 and tail 14 be inert to body fluids and tissue. Such a substance which has been successfully used is silicon rubber. It is also necessary that electrodes 22, 23 and 24, which must connect directly to the outer wall of a nerve or nerve fiber 27, be of a material inert to body fluids and tissue and not be harmful to the outer wall of the nerve to which they are attached. Such a material which has been successfully used is platinum. Another material which may also be used is stainless steel. It should be noted that all mention of materials herein are merely exemplary and not intended to so limit the scope of this invention.

As stated above, leads 26 and 28 must also be of material inert to body fluids and tissue. It is desirable, but is not mandatory, that leads 26 and 28 be of the same material as electrodes 22, 23 and 24.

The leads in the embodiment described herein are disclosed as being coiled lengths of a material, to facilitate ease of flexibility. This has proven to be a highly desirable type of lead structure, but it is not intended that this entire invention be limited to such a lead structure.

While it is necessary that a portion of electrodes 22, 23 and 24 not be encapsulated in the substance of head 12, so that electrodes may be connected to nerve 27, it is highly undesirable to leave the electrodes completely exposed after connection to the nerve. To overcome this problem the embodiments of this invention provide upper layer 15. As shown in FIGURES 2, 4 and 5, upper layer 15 is separated from lower layer 13 only by the width of slot 21. When electrodes 22, 23 and 24 have been connected to nerve 27, upper layer 15 may be fastened upon them by means such as sutures 29. Groove 20 in member 13 is shaped generally to the configuration of nerve 27, and also facilitates firm fastening and insulation of the connection of the electrode to the nerve.

The source of electrical signal energy 11, shown in FIGURE 1, may be a transistorized blocking oscillator powered by a long-life rechargeable battery, which provides a pulse at a predetermined frequency to the nerve 27. Though the source 11 is here shown as being implantable, that is, encapsulated in a substance inert to body fluids and tissue for implanation in the body of an animal, it is not mandatory that the electrode apparatus of this invention be used with an implantable source of electrical signal energy. Tail 14, including leads 26 and 28, may extend from within the body to a point external [of] *to* the body, and be connected to any one of a number of sources of electrical signal energy. Also, the leads may extend to a circuit implanted in the body but powered from a source external to the body.

The advantage of the operation of the electrodes of this invention, in greatly decreasing stray current flow through surrounding body fluids, may best be understood by reference to FIGURE 4, showing the three aligned electrodes 22, 23 and 24. Assume first that electrode 23 were not present, as is the case in the above described application Ser. No. 512,981. Assume also that electrodes 22 and 24 are electrically connected such that current flow is from electrode 22 to electrode 24. In that case, when a signal pulse is applied across the electrodes, current will flow from electrode 22 to the left through nerve 27 to electrode 24 and out through lead 28. However, a certain amount of current will also flow from electrode 22 to the right, and through the body fluids and tissue around head 12 and back into the left side opening of groove 20 to electrode 24. This stray current flow is highly undesirable, especially because of the possibility of stimulating adjacent nerves.

Looking again at the configuration of FIGURE 4 it can be seen that the guarding of active electrode 22 with the additional electrode 23 will greatly decrease the stray current flow through body fluids and tissue. Now the current which attempts to flow to the right from electrode 22 will prefer to flow through electrode 23 and back through lead 28, rather than continue outside around head 12 to the other side of electrode 24.

Lab tests have been conducted upon the electrode apparatus and they have been successful in increasing the maximum limitation on signal energy applied to the electrodes by a factor of approximately 4 or 5. In the laboratory embodiments successfully tested, silicon rubber was used as a substance to encapsulate the leads and electrodes. In one embodiment the electrodes were made of platinum, while the leads were made of coiled lengths of stainless steel.

It is apparent from the foregoing description that the apparatus of this invention provides a novel improved structure, in the form of an implantable electrode, for connection of a source of signal energy to a nerve for providing artificial stimulation of that nerve by timed electrical pulses from a source of signal energy.

It is apparent that the particular configuration of the embodiment described above is only that of a preferred embodiment, and that the guarded implantable electrode of this invention is not limited merely to the specific embodiment described.

The embodiments of the invention in which an exclusive property or privilege is claimed are defined as follows:

1. Medical apparatus for implantation into the body of an animal comprising: first and at least two further electrodes of an electrically conductive material substantially inert to body fluids and tissue; first and second leads of said material connected, respectively, to said first and further electrodes, and adapted to be connected to a source of electrical signal energy; a first portion of said first and further electrodes and said first and second leads being encapsulated in an electrically insulating substance substantially inert to body fluids and tissue; a second portion of said first and further electrodes adapted to be connected to spaced points along a nerve in the body of an animal, for stimulation of the nerve upon receipt of a signal from the source of signal energy; said first electrode connected to be electrically active with respect to said further electrodes; and said electrodes mounted such that said further electrodes are in current guarding relation to said first electrode, to limit stray current flow through body fluids and tissue.

2. The medical apparatus of claim 1 including: a further member of said substance for fastening over said second portion of said first and further electrodes when connected to the nerve.

3. Electrode apparatus implantable in the body of an animal for stimulation of a nerve comprising: a housing of an electrically insulating substance substantially inert to body fluids and tissue, said housing having a head and a tail; a slot in said head dividing a part of said head into an upper layer *and* [an] a lower layer; a groove in said lower layer adjacent said slot; a plurality of electrodes of an electrically conductive material substantially inert to body fluids and tissue, and encased in said head of said housing in spaced relation to one another such that a first of said electrodes lies between others of said electrodes; a portion of each of said electrodes formed to and fitted in said groove, said portions adapted to be connected to spaced points on a nerve in the body of an animal; a pair of leads of said material encased in said tail of said housing; and a first of said pair of leads connected to said first of said electrodes and a second of said pair of leads connected to said others of said electrodes, for connecting said electrodes to a source of signal energy for stimulating the nerve.

4. The electrode apparatus of claim 3 in which said top layer of said housing is adapted to be fastened to said lower layer to hold and shield the nerve in contact with said pair of electrodes.

5. Electrode apparatus implantable in the body of an animal for stimulation of a nerve comprising: first, second and third electrodes of an electrically conductive material substantially inert to body fluids and tissue; said electrodes lying in parallel spaced relation, said second electrode lying between said first and third electrodes; first and second leads of said material, said first lead connected to said first and third electrodes, said second lead connected to said second electrode, for connecting said electrodes to a source of electrical signal energy; encapsulating means of an electrically insulating substance substantially inert to body fluids and tissue encapsulating said electrodes and said leads; and a portion of each of said electrodes being exposed through said encapsulating means for connection to spaced points on a nerve.

6. The apparatus of claim 5 including: a further integral member of said substance for fastening over said exposed portions of said electrodes after connection thereof to the nerve.

*7. Medical apparatus for implantation into the body of an animal comprising: first and at least two further electrodes of an electrically conductive material substantially inert to body fluids and tissue; first and second leads of an electrically conductive material substantially inert to body fluids and tissue connected, respectively, to said first and further electrodes, and adapted to be connected to a source of electrical signal energy; a first portion of said first and further electrodes and said first and second leads being encapsulated in an electrically insulating substance substantially inert to body fluids and tissue; a second portion of said first and further electrodes adapted to be connected to spaced points along a nerve in the body of an animal, for stimulation of the nerve upon receipt of a signal from the source of signal energy; said first electrode connected to be electrically active with respect to said further electrodes; and said electrodes mounted such that said further electrodes are in current guarding relation to said first electrode, to limit stray current flow through body fluids and tissue.*

*8. The medical apparatus of claim 7 including: a further member of said substance for fastening over said second portion of said first and further electrodes when connected to the nerve.*

*9. Electrode apparatus implantable in the body of an animal for stimulation of a nerve comprising: a housing of an electrically insulating substance substantially inert to body fluids and tissue, said housing having a head and a tail; a slot in said head dividing a part of said head into an upper layer and a lower layer; a groove in said lower layer adjacent said slot; a plurality of electrodes of an electrically conductive material substantially inert to body fluids and tissue, and encased in said head of said housing in spaced relation to one another such that a first of said electrodes lies between others of said electrodes; a portion of each of said electrodes formed to and fitted in said groove, said portions adapted to be connected to spaced points on a nerve in the body of an animal; a pair of leads of an electrically conductive material substantially inert to body fluids and tissue encased in said tail of said housing; and a first of said pair of leads connected to said first of said electrodes and a second of said pair of leads connected to said others of said electrodes, for connecting said electrodes to a source of signal energy for stimulating the nerve.*

*10. The electrode apparatus of claim 9 in which said top layer of said housing is adapted to be fastened to said lower layer to hold and shield the nerve in contact with said pair of electrodes.*

*11. Electrode apparatus implantable in the body of an animal for stimulation of a nerve comprising: first, second and third electrodes of an electrically conductive material substantially inert to body fluids and tissue; said electrodes lying in parallel spaced relation, said second electrode lying between said first and third electrodes; first and second leads of an electrically conductive material substantially inert to body fluids and tissue, said first lead connected to said first and third electrodes, said second lead connected to said second electrode, for connecting said electrodes to a source of electrical signal energy; encapsulating means of an electrically insulating substance substantially inert to body fluids and tissue encapsulating said electrodes and said leads; and a portion of each of said electrodes being exposed through said encapsulating means for connection to spaced points on a nerve.*

*2. The apparatus of claim 11 including: a further integral member of said substance for fastening over said exposed portions of said electrodes after connection thereof to the nerve.*

References Cited

The following references, cited by the Examiner, are of record in the patented file of this patent or the original patent.

UNITED STATES PATENTS

| | | | |
|---|---|---|---|
| 3,157,181 | 11/1964 | McCarty | 128—404 |
| 3,348,548 | 10/1967 | Chardack | 128—418 |
| 3,216,424 | 11/1965 | Chardack | 128—418 |
| 1,679,245 | 7/1928 | Gaertner | 128—418 X |
| 3,279,468 | 10/1966 | Levine | 128—410 |

OTHER REFERENCES

Glass et al.: "American Heart Journal," vol. 67, No. 1, January 1964. pp. 137–139.

WILLIAM E. KAMM, Primary Examiner